United States Patent
He et al.

(10) Patent No.: US 9,192,926 B2
(45) Date of Patent: Nov. 24, 2015

(54) METHOD FOR ENHANCING HETEROGENEOUS ASYMMETRIC SELECTIVITY AND CATALYTIC ACTIVITY

(75) Inventors: Jing He, Beijing (CN); Huimin Shi, Beijing (CN); Jiuzhao Wang, Beijing (CN)

(73) Assignee: BEIJING UNIVERSITY OF CHEMICAL TECHNOLOGY, Beijing (CN)

( * ) Notice: Subject to any disclaimer, the term of this patent is extended or adjusted under 35 U.S.C. 154(b) by 927 days.

(21) Appl. No.: 13/316,187

(22) Filed: Dec. 9, 2011

(65) Prior Publication Data
US 2012/0322647 A1 Dec. 20, 2012

(30) Foreign Application Priority Data
Jun. 16, 2011 (CN) .......................... 2011 1 0162128

(51) Int. Cl.
| | |
|---|---|
| B01J 21/00 | (2006.01) |
| B01J 23/00 | (2006.01) |
| B01J 25/00 | (2006.01) |
| B01J 29/00 | (2006.01) |
| B01J 31/00 | (2006.01) |
| B01J 27/24 | (2006.01) |
| B01J 31/02 | (2006.01) |
| C07C 201/12 | (2006.01) |
| C07D 301/19 | (2006.01) |
| B01J 37/03 | (2006.01) |
| B01J 37/30 | (2006.01) |

(52) U.S. Cl.
CPC ........... *B01J 31/0238* (2013.01); *C07C 201/12* (2013.01); *C07D 301/19* (2013.01); *B01J 37/03* (2013.01); *B01J 37/30* (2013.01); *B01J 2231/72* (2013.01); *B01J 2531/0275* (2013.01)

(58) Field of Classification Search
USPC .......................... 502/100, 150, 151, 170, 200
See application file for complete search history.

(56) References Cited

U.S. PATENT DOCUMENTS

2005/0260271 A1 * 11/2005 Bringley ................ A61K 47/02
424/489

FOREIGN PATENT DOCUMENTS

| | | | | |
|---|---|---|---|---|
| EP | 2044992 A1 | * | 4/2009 | ............... C07K 1/16 |
| JP | 2003226681 A | * | 8/2003 | |
| JP | 2005239980 A | * | 9/2005 | |
| JP | 2006281154 A | * | 10/2006 | |

* cited by examiner

*Primary Examiner* — James McDonough
(74) *Attorney, Agent, or Firm* — Hamre, Schumann, Mueller & Larson, P.C.

(57) ABSTRACT

A method for enhancing heterogeneous asymmetric selectivity and catalytic activity belongs to the field of catalytic asymmetric organic synthesis technology, the preparation method of the invention are as follows: firstly preparing the chiral L-amino acids intercalated LDHs by coprecipitation or ion-exchange method; exfoliating the chiral L-amino acids intercalated LDHs into dispersed system of chiral L-amino acids attached to the inorganic LDH nanosheets; then coordinating the L-amino acids in the above dispersed systems with the metal centers for different types of asymmetric catalytic reactions. The results show that the as-prepared catalyst can enhance the asymmetric selectivity effectively. Compared with the homogeneous counterparts under the same reaction conditions, the catalyst exhibits relatively higher yields and largely improves the selectivity of the asymmetric reaction products; and thus the chiral compounds with a higher optical purity can be obtained.

9 Claims, 1 Drawing Sheet

METHOD FOR ENHANCING HETEROGENEOUS ASYMMETRIC SELECTIVITY AND CATALYTIC ACTIVITY

FIELD OF THE INVENTION

The present invention belongs to the field of asymmetric catalytic organic synthesis technology, and particularly provides a method for enhancing heterogeneous asymmetric selectivity and catalytic activity.

BACKGROUND OF THE INVENTION

In recent years, with the development of medicinal chemistry and biochemistry, the demand for optically active organic compounds has been largely growing. This is because many new, high-effective drugs belong to optically active compounds with chiral centers; on the other hand, studies on these drugs show that only one type of optical isomer with certain configuration has the pharmacological activity; while another type of optical isomer may have no any pharmacological activity, and even have toxic or side effects to human beings. One way to get optically pure active enantiomers is the resolution of racemates, whereas the operation of this method is extremely cumbersome, and only a small amount can be handled; Another way is utilization of asymmetric synthesis, which can directly obtain optically active compound with a single configuration. Asymmetric catalysis has been received increasing attention due to its simple process and high efficiency. Recently, many new types of chiral transition metal complexes with high catalytic activity and stereoselectivity have been successfully synthesized, which largely improve the chemical and optical yields of chiral products. Therefore, asymmetric catalysis exhibits a broad prospect and a great power in the synthesis of optically active compounds.

So far, most of the asymmetric reactions are catalyzed by homogeneous catalysts, and the catalysts are mostly chiral transition metal complexes. Amino acids and their derivatives proceed many advantages as the chiral ligands of metal complex catalysts: 1. their structures are easy to be functioned; 2. natural chiral amino acids are cheap and easy to get, and also have a wide range of types; 3. they have a high optical activity and their derivatization are easy to be achieved; 4. the polarization, pH value, and molecular size are easy to modulate; 5. selected metal centers can be in a wide range, and different kinds of metal centers are available in catalyzing different types of asymmetric catalytic reactions, etc. Therefore, studies on using amino acids as chiral ligands have been gradually developed, and good results have been obtained in several respects.

Layered double hydroxides (LDHs), also known as hydrotalcite, are known as a kind of new multifunctional layered materials. Due to its unique characteristics of the composition and structure, such as ordered bi-dimensional layered structure, highly chemical stability, adjustable metal composition in the LDHs layers, exchangeable interlayer anions (a variety of functional anions can be exchanged into the interlayer space). A variety of functional composite materials can thus be constructed. Metal complexes with catalytic properties can be intercalated into LDHs layers by ion-exchange, which avoids multiple steps of covalent ligand modification; moreover, bi-dimensional open space between the adjacent LDH layers is beneficial to take advantage of the interlayer catalysts and exhibit high catalytic activity and selectivity.

SUMMARY OF THE INVENTION

The object in this patent is to supply a method for enhancing heterogeneous asymmetric selectivity and catalytic activity.

The technology scheme involves the preparation of the L-amino acids intercalated LDHs by coprecipitation or ion-exchange methods firstly; exfoliating the chiral L-amino acids intercalated LDHs to obtain chiral L-amino acids attached to the inorganic LDH nanosheets; then coordinating it with the metal centers for kinds of asymmetric catalytic reactions.

The detailed steps of the invention are as follows:

(1) Preparation of chiral L-amino acids intercalated LDHs;

(2) Weighing 0.01~0.03 g of chiral L-amino acids intercalated LDHs obtained in Step (1), which is further exfoliated in formamide (15~30 mL) under $N_2$ condition for 0.5~1.5 h; then shaking the samples in a shaker for 1~8 days with the velocity of 150~250 rpm. The transparent and dispersed system of chiral L-amino acids attached to inorganic LDH nanosheets can be obtained;

(3) Coordinating the chiral L-amino acids attached to inorganic LDH nanosheets obtained in Step (2) with the metal centers for asymmetric catalysis.

The chiral L-amino acids intercalated LDHs are prepared by coprecipitation method as described in Step (1). The detailed steps are as follows:

a. Preparing 0.5~1.5 mol/L of zinc nitrate solution, 0.5~1.5 mol/L of aluminum nitrate solution and 1~25 mol/L of ammonia solution;

b. Weighing the chiral L-amino acids and preparing 50~100 mmol/L solution;

c. Under $N_2$ condition, slowly adding the chiral L-amino acids solution (100~200 mL), aluminum nitrate solution (10~40 mL), and the ammonia solution (5~20 mL) into a four-neck flask and stirring them uniformly; pH value of the system is controlled in the range of 8-12 by adjusting the addition amount of ammonia solution.

d. After adding the solution, the reaction are continued to process for 6~12 h at 25~40° C. under $N_2$ condition; the solid product is washed by dicarbonate and deionized water until the pH value is kept at 7~8; the product is further centrifuged after washed by anhydrous ethanol; then the solid product is dried in vacuum oven for 12~24 h at 30~50° C.; the chiral L-amino acids intercalated LDHs could be obtained and should be stored under the condition of isolation from the air.

The chiral L-amino acids intercalated LDHs are prepared by ion-exchange method as described in Step (1). The detailed steps are as follows:

a. Preparing the nitrate intercalated LDHs precursors;

b. Adjusting the pH value by adding ammonia solution with a concentration of 1~25 mol/L to obtain the chiral L-amino acid salt solution (0.005~0.30 mol/L) with the pH value in the range of 8 to 12;

c. Mixing 0.10~0.20 g of nitrate intercalated LDHs precursors obtained in Step (a) and 10~20 mL of chiral L-amino acid salt solution in Step (b) and stirring for 12~48 h at 20~60° C. under $N_2$ condition; the product is washed by dicarbonate and deionized water until the pH value gets to 7~8; the product is further centrifuged after washed by anhydrous ethanol; then the solid product is dried under vacuum condition at 30~50° C.; the chiral L-amino acids intercalated LDHs can be obtained and should be stored under the condition of isolation from the air.

The formula of the nitrate anion intercalated LDHs precursor is expressed as follows:

$[M^{2+}_{1-x}M^{3+}_x(OH)_2]^{x+}(NO_3^-)_x \cdot mH_2O$, wherein the $M^{2+}$ represents divalent cation, which can be selected in one or more types of $Mg^{2+}$, $Ni^{2+}$, $Co^{2+}$, $Zn^{2+}$, $Mn^{2+}$ and $Cu^{2+}$; preferentially, $M^{2+}$ can be one or more types of $Mg^{2+}$, $Zn^{2+}$ and $Ni^{2+}$; $M^{3+}$ represents trivalent cation, which can be selected in one or more types of $Al^{3+}$, $Cr^{3+}$, $Fe^{3+}$, $Ga^{3+}$ and $In^{3+}$; preferentially, $M^{3+}$ is selected as $Al^{3+}$; x stands for the molar ratio of the $M^{2+}/(M^{3+}+M^{2+})$, and $0.2 \leq x \leq 0.33$; m is the content of the crystalline water, and The as described chiral L-amino acids can be L-alanine (ala), L-serine (ser), L-aspartate (asp) or L-glutamate (glu).

The detailed composition of the chiral L-amino acids attached to inorganic LDH nanosheets is expressed as follows:

$[M^{2+}_{1-x}M^{3+}_x(OH)_2]^{x+}[(A^{a-})_b(XO_3^{c-})_d] \cdot mH_2O$, wherein the $M^{2+}$ represents divalent cation, which can be selected in one or more types of $Mg^{2+}$, $N^{2+}$, $Co^{2+}$, $Zn^{2+}$, $Mn^{2+}$ and $Cu^{2+}$; preferentially, $M^{2+}$ can be one or more types of $Mg^{2+}$, $Zn^{2+}$ and $Ni^{2+}$; $M^{3+}$ represents trivalent cation, which can be selected in one or more types of $Al^{3+}$, $Cr^{3+}$, $Fe^{3+}$, $Ga^{3+}$ and $In^{3+}$; preferentially, $M^{3+}$ is selected as $Al^{3+}$; x stands for the molar ratio of the $M^{2+}/(M^{3+}+M^{2+})$, and $0.2 \leq x \leq 0.33$; A stands for chiral L-amino acid anions, which can be L-alanine (ala), L-serine (ser), L-aspartate (asp) or L-glutamate (glu); a is the negative charge number of chiral L-amino acid anions, a=1 or 2; b is the content of the L-amino acids chiral anions. $XO_3^{c-}$ is the co-intercalated anion of the L-amino acids intercalated LDHs; the $XO_3^{c-}$ can be nitrate or carbonate anion; c is the negative charge number of the co-intercalated anion, c=1 or 2; d is the content of the co-intercalated anions; m is the content of the crystalline water, and $0.1 \leq m \leq 0.8$; in the above formula, ab+cd=x.

The as described metal center can be one or more types of zinc, copper, cobalt, vanadium, titanium, iron; preferentially, metal center is selected as zinc or vanadium.

The as described asymmetric synthesis is asymmetric aldol reaction; i.e., chiral L-amino acids attached to inorganic LDH nanosheets coordinate with the metal center to catalyze asymmetric aldol reaction. The detailed method is described below: exfoliating the chiral L-amino acids intercalated LDHs in formamide to obtain a highly dispersed system of chiral L-amino acids attached to inorganic LDH nanosheets; adding 0.0033~0.0165 mmol of zinc acetate or diethyl zinc into 5-15 mL of the dispersed system, wherein the molar ratio of chiral L-amino acids to zinc is in the range of 1:1 to 5:1; adding 2.0~10.0 mmol of cyclohexanone, 0.011~0.055 mmol of nitrobenzaldehyde into the systems, and the asymmetric reaction is then processed for 12~24 h at 25~40° C.; adding 1~15 mL of saturated sodium chloride solution, then extracting the solution by ethyl acetate for 2 or 3 times; drying the product with anhydrous sodium sulfate for 0.5~2 h; removing the ethyl acetate under vacuum distillation condition; dissolving the resulting product by 1~2 mL of methanol solution and detecting the conversion of the reactants and the enantioselectivity of the products by HPLC.

The as described asymmetric synthesis is asymmetric epoxidation reaction; i.e., chiral L-amino acids attached to inorganic LDH nanosheets coordinate with the metal center to catalyze asymmetric epoxidation reaction. The detailed method is described below: exfoliating the chiral L-amino acids intercalated LDHs in formamide to obtain a highly dispersed system of chiral L-amino acids attached to inorganic LDH nanosheets; adding 1~2 mL of dichloromethane, and then adding 0.01~0.21 mol of vanadium isopropyl or vanadyl sulfate; the molar ratio of the chiral L-amino acids to vanadium is in the range of 0.5:1 to 7:1; stirring the solution at 0~20° C. for 2~4 h; then adding 0.2~2 mL of methylene chloride containing 0.83~2.33 mmol tertbutyl hydroperoxide (TBHP) and 0.55~1.55 mmol of allyl alcohol solution; stirring the solution for 8~48 h at ambient temperature, then stopping the reaction by adding 0.5~3.0 mL saturated sodium sulfite solution; extracting the solution by anhydrous ether for 2 or 3 times; drying the product with anhydrous sodium sulfate for 0.5~2 h; the product is further purified and obtained by using of column chromatography with the eluent of ethyl acetate to n-hexane (1:21:3); calculating the conversion of reactants, the yield and the enantioselectivity of products by HPLC.

By using electrostatic interaction, this invention has achieved the introduction of the chiral L-amino acids into the interlayer space of bi-dimensional ordered LDHs; L-amino acids intercalated LDHs can be exfoliated in formamide. Coordinating the exfoliated chiral L-amino acids attached to inorganic LDH nanosheets with the metal centres can be used to enhance the asymmetric selectivity in many types of asymmetric catalytic reactions. Compared with the homogeneous counterpart, the catalyst exhibits relatively higher yields and better enantioselectivity of asymmetric products. For catalyzing asymmetric aldol reaction, using the typical homogeneous catalyst, 73% yield and 6% e.e. value of the trans-products can be obtained; whereas similar yield but 80% e.e. value of the trans- products can be obtained by using the catalyst prepared in this invention in the same reaction time. For catalyzing asymmetric epoxidation reaction, using the typical homogeneous catalyst, 16% e.e. value of the cis-products and 53% e.e. value of the trans-products can be obtained with a 99% yield of epoxidation products; whereas 93% yield, 63% e.e. value of the cis- products and 96% e.e. value of the trans-products can be obtained by using chiral L-amino acids attached to inorganic LDH nanosheets in the same reaction time.

BRIEF DESCRIPTION OF THE DRAWINGS

XRD patterns of the chiral L-amino acids intercalated LDHs are shown in FIG. 1: (a) Zn—Al-ala-LDHs, (b) Zn—Al-ser-LDHs, (c) Zn—Al-asp-LDHs, (d) Zn—Al-NO₃-LDHs, (e) Zn—Al-glu-LDHs.

The photographs of the chiral L-amino acids intercalated LDHs and their exfoliated states are shown in FIG. 2. (1) Zn—Al-ala-LDHs, (2) Zn—Al-ser-LDHs, (3) Zn—Al-asp-LDHs, (4) Zn—Al-glu-LDHs; (a) L-amino acids intercalated LDHs dispersed in formamide; (b) L-amino acids intercalated LDHs exfoliated in formamide; (c) Tyndall effect of the exfoliated system.

DETAILED DESCRIPTION OF THE EMBODIMENTS

Figures 1, 2:
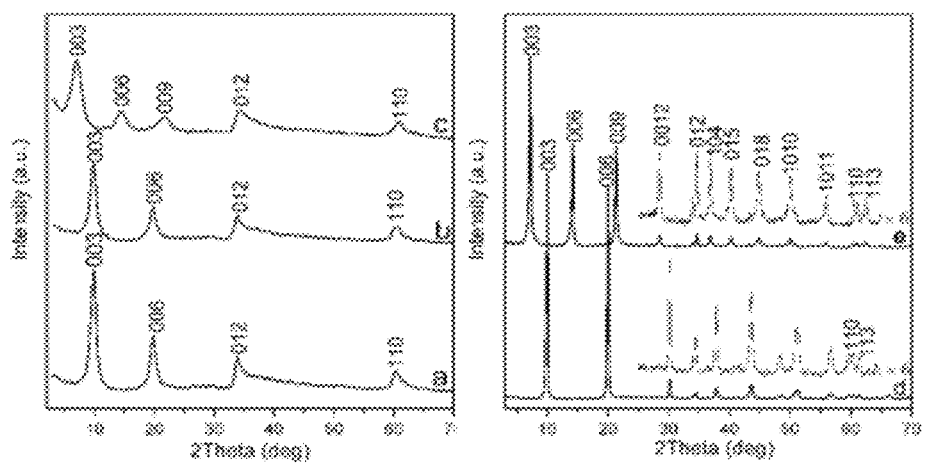

The present invention will be further explained through following examples:

Example 1

A. Preparing 20 mL of $Zn(NO_3)_2$ solution (0.5 M), 10 mL of $Al(NO_3)_3$ solution (0.5 M); 100 mL of L-alanine solution (50 mM), and ammonia solution (1 M). Under $N_2$ condition, adding the L-alanine solution, zinc nitrate solution, aluminum nitrate solution and ammonia solution slowly into a four-neck flask while stirring the solution. Adjusting the pH value to 10 by addition of 1 M ammonia solution; After adding the solution, the reaction was further processing for 6 h at 40° C. under $N_2$ condition; After centrifugation, the solid product was washed by dicarbonate and deionized water and anhydrous ethanol; then the solid product was dried under vacuum condition for 24 h at ambient temperature; the L-alanine intercalated LDHs can be obtained, which was denoted as Zn—Al-ala-LDHs.

B. Adding 0.03 g of the obtained L-alanine acids intercalated LDHs into 30 mL of formamide; under $N_2$ condition, stirring the solution for 0.5 h; then shaking the samples in a shaker for 1 day at 25° C. with the velocity of 200 rpm. The transparent and dispersed systems of chiral L-alanine attached to inorganic LDH nanosheets can be obtained. The detailed composition of the product is $[Zn^{2+}_{1-x}Al^{3+}_{x}(OH)_2]^{x+}[(ala^-)_b(NO_3^-)_d]\cdot mH_2O$, x=0.39, b=0.13, d=0.26, m=0.42. Sealing and storing the product.

Example 2

A. Preparing 10 mL of $Zn(NO_3)_2$ solution (1.5 M), 5 mL of $Al(NO_3)_3$ solution (1.5 M); 100 mL of L-serine solution (100 mM), and ammonia solution (1 M). Under $N_2$ condition, adding the L-serine solution, zinc nitrate solution, aluminum nitrate solution and ammonia solution slowly into a four-neck flask while stirring the solution. Adjusting the pH value to 10 by addition of 1 M ammonia solution; After adding the solution, the reaction was further processing for 8 h at 40° C. under $N_2$ condition; After centrifugation, the product was washed by dicarbonate and deionized water and anhydrous ethanol; then the solid product was dried under vacuum condition for 24 h at ambient temperature; the L-serine intercalated LDHs can be obtained, which was denoted as Zn—Al-ser-LDHs.

B. Adding 0.02 g of the obtained L-serine acids intercalated LDHs into 20 mL of formamide solution; under $N_2$ condition, stirring the solution for 0.5 h; then shaking the samples in a shaker for 3 days at 25° C. with the velocity of 200 rpm. The transparent and dispersed systems of chiral L-serine attached to inorganic LDH nanosheets can be obtained. The detailed composition of the product is $[Zn^{2+}_{1-x}Al^{3+}_{x}(OH)_2]^{x+}[(ser^-)_b(NO_3^-)_d]\cdot mH_2O$, x=0.37, b=0.13, d=0.24, m=0.24. Sealing and storing the product.

Example 3

A. Preparing 40 mL of $Zn(NO_3)_2$ solution (1 M), 20 mL of $Al(NO_3)_3$ solution (1M); 100 mL of L-aspartate solution (100 mM), and ammonia solution (1 M). Under $N_2$ condition, adding the L-aspartate solution, zinc nitrate solution, aluminum nitrate solution and ammonia solution slowly into a four-neck flask while stirring the solution. Adjusting the pH value to 10 by addition of 1 M ammonia solution; After adding the solution, the reaction was further processing for 12 h at 40° C. under $N_2$ condition; After centrifugation, the product was washed by dicarbonate and deionized water and anhydrous ethanol; then the solid product was dried under vacuum condition for 24 h at ambient temperature; the L-aspartate intercalated LDHs can be obtained, which was denoted as Zn—Al-asp-LDHs.

B. Adding 0.03 g of the obtained L-aspartate intercalated LDHs into 30 mL of formamide solution; under $N_2$ condition, stirring the solution for 0.5 h; then shaking the samples in a shaker for 3 days at 25° C. with the velocity of 200 rpm. The transparent and dispersed systems of the L-aspartate attached to inorganic LDH nanosheets can be obtained. The detailed composition of the product is $[Zn^{2+}_{1-x}Al^{3+}_{x}(OH)_2]^{x+}[(asp^{2-})_b(NO_3^-)_d]\cdot mH_2O$, x=0.36, b=0.17, d=0.21, m=0.04. Sealing and storing the product.

Example 4

A. Adding 0.01 mol of $Zn(NO_3)_2\cdot 6H_2O$, 0.005 mol of $Al(NO_3)_3\cdot 9H_2O$ and 0.035 mol of urea into 320 mL of deionized water to dissolve; removing the solution to a three-neck flask, stirring and refluxing for 24 h; After the reaction, the product was filtered and further washed with deionized water to pH of 7; then washed with anhydrous ethanol once to make the product dispersed; drying the product at 60° C. in the oven, the solid powder can be obtained, which was denoted as $Zn_2Al$—$CO_3$-LDHs.

B. Adding 0.40 g of the obtained $Zn_2Al$—$CO_3$-LDHs into 400 mL of $NaNO_3$ solution (1.5 mol/L), then adding 0.002 mol of concentrated $HNO_3$, stirring the solution for 48 h at ambient temperature under $N_2$ condition; After the reaction, the product was filtered and further washed with deionized water to pH at 7; then washed with anhydrous ethanol once to make the product dispersed; drying the product at 25° C. in the oven, the solid powder, $NO_3^-$ intercalated LDHs can be obtained, which was denoted as Zn—Al—$NO_3$-LDHs. The chemical formula is $[Zn^{2+}_{1-x}Al^{3+}_{x}(OH)_2]^{x+}(NO_3^-)_x\cdot mH_2O$, x=0.33, m=1.2;

C. Adjusting the pH value by ammonia solution (25 mol/L) to obtain 15 mL of chiral L-glutamate salt solution (0.086 mol/L, pH=10.25); adding 0.19 g of Zn—Al—$NO_3$-LDHs precursor obtained in step (B); stirring the solution for 48 h at 50° C. under $N_2$ condition; after the reaction, the product was washed with deionized water and ethanol; after centrifugation, drying the sample at 25° C. under vacuum condition, the product L-glutamate intercalated LDHs can be obtained, denoted as Zn—Al-glu-LDHs; preserving the sample under vacuum and drying condition.

D. Weighting 0.02 g of the obtained Zn—Al-glu-LDHs into 30 mL of formamide solution; under $N_2$ condition, stirring the solution for 0.5 h; then shaking the samples in a shaker for 8 days at 30° C. with the velocity of 250 rpm. The transparent and dispersed system of chiral L-glutamate attached to inorganic LDH nanosheets can be obtained. The detailed composition of the product is $[Zn^{2+}_{1-x}Al^{3+}_{x}(OH)_2]^{x+}[(glu^{2-})_b(CO_3^{2-})_d]\cdot mH_2O$, x=0.40, b=0.17, d=0.03, m=0.78. Sealing and storing the product.

Application Example 1

Weighting and mixing 407 μL of cyclohexanone (2.0 mmol), 0.0083 g of nitrobenzaldehyde (0.055 mmol), 10 mL of dispersed systems of chiral L-glutamate attached to inorganic LDH nanosheets obtained from example 4, and 0.0020 g of zinc acetate (0.011 mmol) to react at 25° C. for 12 h; after the reaction, removing the system into the separating funnel and adding 5 mL of saturated sodium chloride solution, then adding 15 mL of ethyl acetate for extraction; the aqueous phase was added with 5 mL of deionized water, and washed with 15 mL of ethyl acetate twice. Combining the organic phases and drying the system by anhydrous sodium sulfate for 0.5 h, and removing the ethyl acetate by reduced pressure distillation; dissolving the obtained product by addition of 1 mL methanol; the conversion of the reactants was detected as 76% and the e.e. value of trans-product (2-[hydroxy-(4-nitrophenyl)-methyl]-cyclohexanone) was 72% by HPLC technique.

Comparation Example 1

Weighting and mixing 407 μL of cyclohexanone (2.0 mmol), 0.0083 g of nitrobenzaldehyde (0.055 mmol), 0.055 mmol of L-glutamate, and 0.011 mmol of zinc acetate to react at 25° C. for 12 h; after the reaction, removing the system into the separating funnel and adding 5 mL of saturated sodium chloride solution, then adding 15 mL of ethyl acetate for extraction; the aqueous phase was added with 5 mL of deionized water, and washed with 15 mL of ethyl acetate twice. Combining the organic phases and drying the system by anhydrous sodium sulfate for 0.5 h, and removing the ethyl acetate by reduced pressure distillation; dissolving the obtained product by addition of 1 mL methanol; the conversion of the reactants was detected as 72% and the e.e. value of trans-product (2-[hydroxy-(4-nitro-phenyl)-methyl]-cyclohexanone) was measured as 3% by HPLC technique.

Application Example 2

Weighting and mixing 407 μL of cyclohexanone (2.0 mmol), 0.0083 g of nitrobenzaldehyde (0.055 mmol), 10 mL of dispersed systems of chiral L-aspartate attached to inorganic LDH nanosheets obtained from example 3, and 0.0020 g of zinc acetate (0.011 mmol) to react at 25° C. for 12 h; after the reaction, removing the system into the separating funnel and adding 5 mL of saturated sodium chloride solution, then adding 15 mL of ethyl acetate for extraction; the aqueous phase was added with 5 mL of deionized water, and washed with 15 mL of ethyl acetate twice. Combining the organic phases and drying the system by anhydrous sodium sulfate for 0.5 h, and removing the ethyl acetate by reduced pressure distillation; dissolving the obtained product by addition of 1 mL methanol; the conversion of the reactants was detected as 73% and the e.e. value of trans-product (2-[hydroxy-(4-nitro-phenyl)-methyl]-cyclohexanone) was measured as 80% by HPLC technique.

Comparation Example 2

Weighting and mixing 407 μL of cyclohexanone (2.0 mmol), 0.0083 g of nitrobenzaldehyde (0.055 mmol), 0.055 mmol of L-aspartate, and 0.0020 g of zinc acetate (0.011 mmol) to react at 25° C. for 12 h; after the reaction, removing the system into the separating funnel and adding 5 mL of saturated sodium chloride solution, then adding 15 mL of ethyl acetate for extraction; the aqueous phase was added with 5 mL of deionized water, and washed with 15 mL of ethyl acetate twice. Combining the organic phases and drying the system by anhydrous sodium sulfate for 0.5 h, and removing the ethyl acetate by reduced pressure distillation; dissolving the obtained product by 1 mL of methanol; the conversion of the reactants was detected as 73% and the e.e. value of trans-product (2-[hydroxy-(4-nitro-phenyl)-methyl]-cyclohexanone) was measured as 6% by HPLC technique.

Application Example 3

Adding 1 mL of methylene chloride and 0.0104 mmol of vanadate isopropyl (VO(O-i-Pr)$_3$) into 21 mL of dispersed system of chiral L-alanine acids attached to inorganic LDH nanosheets obtained from example 1, stirring the solution for 2 h at 20° C.; then adding 0.60 mL of methylene chloride containing 1.59 mmol TBHP and 1.05 mmol of allyl alcohol solution; stirring the solution for 520 minutes at ambient temperature, then adding 1 mL of saturated Na$_2$SO$_3$ to terminate the reaction; adding anhydrous ether to extract for 3 times; drying the sample for 0.5 h by anhydrous Na$_2$SO$_4$; the product was purified and obtained by the use of column chromatography with the eluent volume ratio of ethyl acetate to n-hexane of 1:2; the yield of products (2,3-epoxy-,2~methyl-3-benzene-1-propanol) was measured as 93%; the e.e. values for the cis- and trans- products were detected as 63% and 96% by HPLC technique.

Comparation Example 3

Adding 0.0210 mmol L-alanine into 21 mL of formamide, then adding 1 mL of methylene chloride and 0.0104 mmol of vanadate isopropyl (VO(O-i-Pr)$_3$) into the system, stirring the solution for 2 h at 20° C.; then adding 0.60 mL of methylene chloride containing 1.59 mmol TBHP and 1.05 mmol of allyl alcohol solution; stirring the solution for 520 minutes at ambient temperature, then adding 1 mL of saturated Na$_2$SO$_3$ to terminate the reaction; adding anhydrous ether to extract for 3 times; drying the sample for 0.5 h by anhydrous Na$_2$SO$_4$; the product was purified and obtained by the use of column chromatography with the eluent volume ratio of ethyl acetate to n-hexane of 1:2; the yield of products (2,3-epoxy-,2~methyl-3-benzene-1-propanol) was measured as 93%;, the e.e. values for the cis- and trans- products were detected as 63% and 96% by HPLC technique.

Application Example 4

Adding 1 mL of methylene chloride and 0.0210 mmol of vanadyl sulfate (VOSO$_4$) into 19 mL of the dispersed system of chiral L-serine acids attached to inorganic LDH nanosheets obtained from example 2, stirring the solution for 2 h at 20° C.; then adding 0.60 mL of methylene chloride containing 1.59 mmol TBHP and 1.05 mmol of allyl alcohol solution; stirring the solution for 12 h at ambient temperature, then adding 2 mL of saturated Na$_2$SO$_3$ to terminate the reaction; adding anhydrous ether to extract for 3 times; drying the sample for 0.5 h by anhydrous Na$_2$SO$_4$; the product was purified and obtained by the use of column chromatography with the eluent volume ratio of ethyl acetate to n-hexane of 1:2; the yield of products (2,3-epoxy-,2-methyl-3-benzene-1-propanol) was measured as 93%; the e.e. values for the cis- and trans- products were detected as 60% and 99% by HPLC technique.

Comparation Example 4

Adding 0.0210 mmol of L-serine into 19 mL formamide, 1 mL of methylene chloride and 0.0210 mmol of vanadyl sulfate (VOSO$_4$) into the solution, stirring the solution for 2 h at 20° C.; then adding 0.60 mL of methylene chloride containing 1.59 mmol TBHP and 1.05 mmol of allyl alcohol solution; stirring the solution for 12 h at ambient temperature, then adding 3 ml, of saturated Na$_2$SO$_3$ to terminate the reaction; adding anhydrous ether to extract for 3 times; drying the sample for 0.5 h by anhydrous Na$_2$SO$_4$; the product was purified and obtained by the use of column chromatography with the eluent volume ratio of ethyl acetate to n-hexane of 1:2; the yield of products (2,3-epoxy-,2~methyl-3-benzene-1-propanol) was measured as 81%; the e.e. values for the cis- and trans- products were detected as 23% and 14% by HPLC technique.

The invention claimed is:
1. A method for enhancing heterogeneous asymmetric selectivity and catalytic activity, including:
   (1) Preparation of chiral L-amino acids intercalated LDHs;
   (2) Weighing 0.01~0.03 g of chiral L-amino acids intercalated LDHs obtained in Step (1), which is further exfoliated in formamide (15~30 mL) under N$_2$ condition for 0.5~1.5 h;
   then shaking the samples in a shaker for 1~8 days with the velocity of 150~250 rpm; the transparent and dispersed system of chiral L-amino acids attached to inorganic LDH nanosheets can be obtained;
   (3) Coordinating the chiral L-amino acids attached to inorganic LDH nanosheets obtained in Step (2) with the metal centers for asymmetric catalysis.
2. According to the claim 1 of a method for enhancing heterogeneous asymmetric selectivity and catalytic activity, wherein the chiral L-amino acids intercalated LDHs are prepared by coprecipitation method as described in Step (1); the detailed steps are as follows:
  a. Preparing 0.5~1.5 mol/L of zinc nitrate solution, 0.5~1.5 mol/L of aluminum nitrate solution and 1~25 mol/L of ammonia solution;
  b. Weighing the chiral L-amino acids and preparing 50~100 mmol/L solution;
  c. Under $N_2$ condition, slowly adding the chiral L-amino acids solution (100~200 mL), aluminum nitrate solution (10~40 mL), and the ammonia solution (5~20 mL) into a four-neck flask and stirring them uniformly; pH value of the system is controlled in the range of 8~12 by adjusting the addition amount of ammonia solution;
  d. After adding the solution, the reaction are continued to process for 6~12 h at 25~40° C. under $N_2$ condition; the solid product is washed by dicarbonate and deionized water until the pH value is kept at 7~8; the product is further centrifuged after washed by anhydrous ethanol; then the solid product is dried under vacuum oven for 12~24 h at 30~50° C.; the chiral L-amino acids intercalated LDHs could be obtained and should be stored under the condition of isolation from the air.

3. According to the claim 1 of a method for enhancing heterogeneous asymmetric selectivity and catalytic activity, wherein the chiral L-amino acids intercalated LDHs are prepared by ion-exchange method as described in Step (1); the detailed steps are as follows:
  a. Preparation of the nitrate intercalated LDHs precursors;
  b. Adjusting the pH value by adding ammonia solution with a concentration of 1~25 mol/L to obtain the chiral L-amino acid salt solution (0.005~0.30 mol/L) with the pH value in the range of 8 to 12;
  c. Mixing 0.10~0.20 g of nitrate intercalated LDHs precursors obtained in Step (a) and 10~20 mL of chiral L-amino acid salt solution in Step (b) and stirring for 12~48 h at 20~60° C. under $N_2$ condition; the product is washed by dicarbonate and deionized water until the pH value gets to 7~8; the product is further centrifuged after washed by anhydrous ethanol; then the solid product is dried under vacuum condition at 30~50° C.; the chiral L-amino acids intercalated LDHs can be obtained and should be stored under the condition of isolation from the air.

4. According to the claim 3 of a method for enhancing heterogeneous asymmetric selectivity and catalytic activity, wherein the formula of the nitrate anion intercalated LDHs precursor is expressed as follows:

$[M^{2+}_{1-x}M^{3+}_x(OH)_2]^{x+}(NO_3^-)_x \cdot mH_2O$, wherein the $M^{2+}$ represents divalent cation, which can be selected in one or more types of $Mg^{2+}$, $Ni^{2+}$, $Co^{2+}$, $Zn^{2+}$, $Mn^{2+}$ and $Cu^{2+}$; preferentially, $M^{2+}$ can be one or more types of $Mg^{2+}$, $Zn^{2+}$, and $Ni^{2+}$; $M^{3+}$ represents trivalent cation, which can be selected in one or more types of $Al^{3+}$, $Cr^{3+}$, $Fe^{3+}$, $Ga^{3+}$ and $In^{3+}$; preferentially, $M^{3+}$ is selected as $Al^{3+}$; x stand for the molar ratio of the $M^{2+}/(M^{3+}+M^{2+})$, and $0.2 \leq x \leq 0.33$; m is the content of the crystalline water, and $0 \leq m \leq 2$.

5. According to the claim 1 of a method for enhancing heterogeneous asymmetric selectivity and catalytic activity, wherein the described chiral L-amino acids can be L-alanine (ala), L-serine (ser), L-aspartate (asp) or L-glutamate (glu).

6. According to the claim 1 of a method for enhancing heterogeneous asymmetric selectivity and catalytic activity, wherein the detailed composition of the chiral L-amino acids attached to inorganic LDH nanosheets is expressed as follows:

$[M^{2+}_{1-x}M^{3+}_x(OH)_2]^{x+}[(A^{a-})_b(XO_3^{c-})_d] \cdot mH_2O$, wherein the $M^{2+}$ represents divalent cation, which can be selected in one or more types of $Mg^{2+}$, $Ni^{2+}$, $Co^{2+}$, $Zn^{2+}$, $Mn^{2+}$ and $Cu^{2+}$; preferentially, $M^{2+}$ can be one or more types of $Mg^{2+}$, $Zn^{2+}$ and $Ni^{2+}$; $M^{3+}$ represents trivalent cation, which can be selected in one or more types of $Al^{3+}$, $Cr^{3+}$, $Fe^{3+}$, $Ga^{3+}$ and $In^{3+}$; preferentially, $M^{3+}$ is selected as $Al^{3+}$; x stand for the molar ratio of the $M^{2+}/(M^{3+}+M^{2+})$, and $0.2 < x < 0.33$; A stands for chiral L-amino acid anions, which can be L-alanine (ala), L-serine (ser), L-aspartate (asp) or L-glutamate (glu); a is the negative charge number of chiral L-amino acid anions, a=1 or 2; b is the content of the chiral L-amino acid anions. $XO_3^{c-}$ is the co-intercalated anion of the L-amino acids intercalated LDHs; the $XO_3^{c-}$ can be nitrate or carbonate anion; c is the negative charge number of the co-intercalated anion, c=1 or 2; d is the content of the co-intercalated anions; m is the content of the crystalline water, and $0.1 \leq m \leq 0.8$; in the above formula, ab+cd=x.

7. According to the claim 1 of a method for enhancing heterogeneous asymmetric selectivity and catalytic activity, wherein the as described metal center can be one or more types of zinc, copper, cobalt, vanadium, titanium, iron; preferentially, metal center is selected as zinc or vanadium.

8. According to the claim 7 of a method for enhancing heterogeneous asymmetric selectivity and catalytic activity, wherein the as described asymmetric synthesis is asymmetric aldol reaction; i.e., chiral L-amino acids attached to inorganic LDH nanosheets coordinate with the metal center to catalyze asymmetric aldol reaction. The detailed method is described below: exfoliating the chiral L-amino acids intercalated LDHs in formamide to obtain a highly dispersed system of chiral L-amino acids attached to inorganic LDH nanosheets; adding 0.0033~0.0165 mmol of zinc acetate or diethyl zinc into 5-15 mL of the dispersed system, wherein the molar ratio of chiral L-amino acids to zinc is in the range of 1:1 to 5:1; adding 2.0~10.0 mmol of cyclohexanone, 0.011~0.055 mmol of nitrobenzaldehyde into the systems, and the asymmetric reaction is then processed for 1224 h at 25~40° C.; adding 1-15 mL of saturated sodium chloride solution, then extracting the solution by ethyl acetate for 2 or 3 times; drying the product with anhydrous sodium sulfate for 0.5~2 h; removing the ethyl acetate under vacuum distillation condition; dissolving the resulting product by 1~2 mL of methanol solution and detecting the conversion of the reactants and the enantioselectivity of the products by HPLC.

9. According to the claim 7 of a method for enhancing heterogeneous asymmetric selectivity and catalytic activity, wherein the as described asymmetric synthesis is asymmetric epoxidation reaction; i.e., chiral L-amino acids attached to inorganic LDH nanosheets coordinate with the metal center to catalyze asymmetric epoxidation reaction. The detailed method is described below: exfoliating the chiral L-amino acids intercalated LDHs in formamide to obtain a highly dispersed system of chiral L-amino acids attached to inorganic LDH nanosheets; adding 1-2 mL of dichloromethane, and then adding 0.01-0.21 mol of vanadium isopropyl or vanadyl sulfate; the molar ratio of the chiral L-amino acids to vanadium is in the range of 0.5:1 to 7:1; stirring the solution at 0~20° C. for 2~4 h; then adding 0.2~2 mL of methylene chloride containing 0.83~2.33 mmol tertbutyl hydroperoxide (TBHP) and 0.55~1.55 mmol of allyl alcohol solution; stirring the solution for 8~48 h at ambient temperature, then stopping the reaction by adding 0.5~3.0 mL saturated sodium sulfite solution; extracting the solution by anhydrous ether for 2 or 3 times; drying the product with anhydrous sodium sulfate for 0.5~2 h; the product is further purified and obtained by using of column chromatography with the eluent of ethyl acetate to n-hexane (1:2~1:3); calculating the conversion of reactants, the yield and the enantioselectivity of products by HPLC.

* * * * *